United States Patent [19]
Gunkel et al.

[11] Patent Number: 4,556,684
[45] Date of Patent: Dec. 3, 1985

[54] FLAME RETARDANT STYRENE MODIFIED POLYPHENYLENE ETHER RESINS

[75] Inventors: Louis T. Gunkel, Yardley, Pa.; Charles V. Juelke, Belle Mead, N.J.

[73] Assignee: FMC Corporation, Philadelphia, Pa.

[21] Appl. No.: 644,409

[22] Filed: Aug. 27, 1984

[51] Int. Cl.$^4$ .............................................. C08K 5/52
[52] U.S. Cl. ......................................... 524/141; 524/143; 252/400 A; 252/601; 252/609; 525/132
[58] Field of Search ............... 252/400 A, 601, 609; 260/974; 524/141, 143, 508; 525/132

[56] References Cited

U.S. PATENT DOCUMENTS

| | | | |
|---|---|---|---|
| 3,125,529 | 3/1964 | Simmons et al. | 252/49.8 |
| 3,257,357 | 6/1966 | Stamatoff | 528/215 |
| 3,257,358 | 6/1966 | Stamatoff | 528/215 |
| 3,819,759 | 6/1974 | Weaver et al. | 260/860 |
| 3,883,613 | 5/1975 | Cooper | 524/141 |
| 3,890,406 | 6/1975 | Matsunaga et al. | 260/874 |
| 4,077,934 | 3/1978 | Lee, Jr. | 523/307 |
| 4,101,503 | 7/1978 | Cooper et al. | 525/132 |
| 4,446,062 | 5/1984 | Lee et al. | 252/609 |
| 4,448,909 | 5/1984 | Golba, Jr. et al. | 523/303 |

Primary Examiner—John Kight
Assistant Examiner—Kriellion Morgan
Attorney, Agent, or Firm—Robert D. Jackson; Eugene G. Horsky

[57] ABSTRACT

Flame retardant polyphenylene ether resin compositions are described in which the flame retardant agent is a mixture (by weight) of the following:
(a) about 1.5% to about 3.0% of:

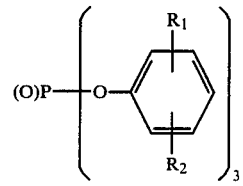

(b) about 15.0% to about 20.0% of:

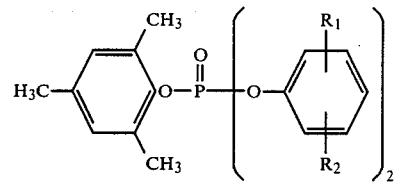

(c) about 23.0% to about 28.0% of:

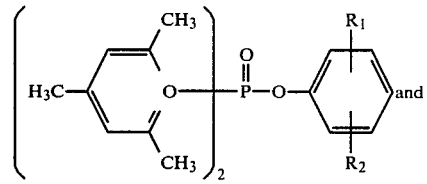

(d) about 47.0% to about 56.0% of:

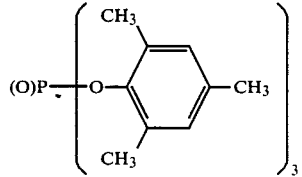

wherein $R_1$ and $R_2$ are each selected from the class consisting of hydrogen, methyl and ethyl, it being understood that when one of $R_1$ and $R_2$ is hydrogen the other is ethyl and when one of $R_1$ and $R_2$ is methyl the other is methyl, the resulting two methyl groups being in the 2,4-, 2,5-, 2,3-, 3,4- and 3,5-positions, it being further understood that the ethyl groups are almost entirely in the meta (m) and para (p) positions.

4 Claims, No Drawings

FLAME RETARDANT STYRENE MODIFIED POLYPHENYLENE ETHER RESINS

This invention relates to certain substituted triphenyl-phosphate esters and their use as flame retardants in thermoplastic polymers, particularly in polyphenylene ether resins.

The polyphenylene ethers are a well-known class of linear thermoplastic engineering resins, the description and preparation of which are documented at length in the technical and patent literature; see U.S. Pat. Nos. 3,306,874 and 3,306,875 to Hay and U.S. Pat. Nos. 3,257,357 and 3,257,358 to Stamatoff. Generally speaking, polyphenylene ethers are combined with other polymers, such as a polystyrene, to provide modified polyphenylene ether resins. An important commercial grade polyphenylene ether engineering plastic consists of about 35 to 85% by weight polyphenylene ether and about 55 to 15% by weight of a polystyrene resin. Such modified polyphenylene ether resins are used extensively in the automotive and transportation industries as a replacement for metal to reduce vehicle weight. Other large-scale users include manufacturers of electrical/electronic equipment and appliances.

Since styrene modified polyphenylene ether resins are combustible, they are customarily formulated with a flame retardant additive of which the triaryl esters of phosphoric acid, particularly triphenyl phosphates, are well-known. Although numerous members of this series have been prepared and tested, none have proved entirely satisfactory. This is not too surprising considering the manifold nature of the problem associated with the development of a satisfactory flame retardant for plastics. In addition to flame suppressing capacity, other standards must be met. Thus, a flame retardant must be heat and light stable, noncorrosive, nontoxic, compatible with and not adversely alter the mechanical properties of the plastic. And, of course, it must meet economic criteria if commercialization is to be realized.

One type of physical deformation that occurs in flame retardant thermoplastic resins, such as the polyphenylene ether compositions or resins mentioned herein, is known as stress cracking. Commonly referred to as juicing in the trade, the flame retardant boils off or exudes during hot molding of the resin and condenses on the mold and the surface of the resin. The plastic part may be under stress as a result of the molding and the condensed flame retardant may result in cracking of the molded part. Failure can occur during molding or on storage of the final manufactured article.

Stress cracking is particularly difficult to control when using organic phosphates as a flame retardant in styrene modified polyphenylene ether resins; in such instances juicing can be quite severe.

It has now been discovered that flame retardant styrene modified polyphenylene resins exhibiting the aforementioned desiderata, particularly as regards resistance to stress cracking, can be realized by using as a flame retardant certain novel mixtures of lower alkyl substituted triphenyl phosphates and the provision of said flame retardant resins constitutes an object of the present invention. It is also an object of the invention to provide the said mixtures of lower alkyl substituted triphenyl phosphates and a method of making same. Other objects and purposes will become manifest subsequently herein.

The lower alkyl substituted triphenyl phosphate mixtures of the invention consist essentially of four types, the identity and percentage by weight of which are set forth below.

1. Trixylenyl Phosphate Ester (XXX)
MW=410 ($C_{24}H_{27}PO_4$) about 1.5 to about 3.0%

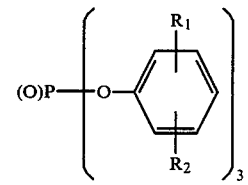

2. Bisxylenyl/mesityl Phosphate Ester (MXX)
MW=424 ($C_{25}H_{29}PO_4$) about 15.0 to about 20.0%

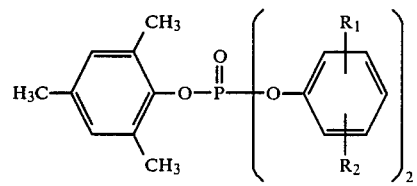

3. Bismesityl/xylenyl Phosphates Ester (MMX)
MW=438 ($C_{26}H_{31}PO_4$) about 23.0 to about 28.0%

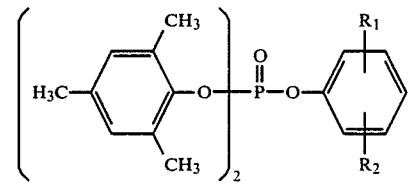

4. Trismesityl Phosphate Ester (MMM)
MW=452 ($C_{27}H_{33}PO_4$) about 47.0 to about 56.0%

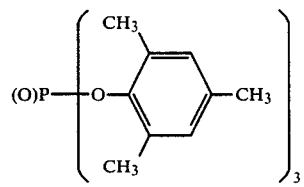

wherein $R_1$ and $R_2$ are each selected from the class consisting of hydrogen, methyl and ethyl, it being understood that when one of $R_1$ and $R_2$ is hydrogen the other is ethyl and when one of $R_1$ and $R_2$ is methyl the other is methyl, the resulting two methyl groups being in the 2,4-, 2,5-, 2,3-, 3,4- and 3,5-positions, it being further understood that the ethyl groups are almost entirely in the meta (m) and para (p) positions. Except for trace amounts, there are no 2,6-xylenyl phosphates. Since either the dimethyl or the ethyl groups give rise to isomeric phenolic moieties, the chemical configuration of each phosphate ester type as depicted in formulas 1, 2 or 3 thus embraces a distribution of position isomers all of which have the same molecular weight and structure.

The lower alkyl substituted phenyl phosphates herein are prepared via a two-stage reaction, Step I of which consists in adding phosphorus oxychloride to mesitol (A) in the presence of aluminum chloride catalyst to form intermediate chloro mesityl phosphates (B) and (C) followed by reaction with a mixture of isomeric xylenols having methyl and ethyl substituents as above defined for $R_1$ and $R_2$. The course of Step I proceeds in accordance with the following scheme:

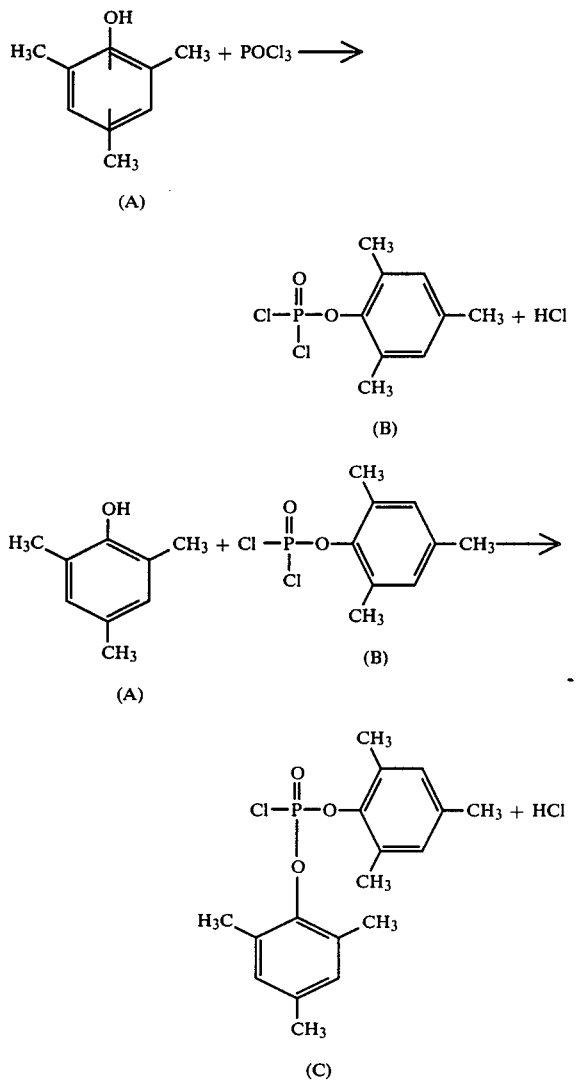

STEP I

Step I is continued until all of the phosphorodichloridate (B) is depleted and only phosphorochloridate (C) plus a minor about of trimesityl phosphate remain. The course of Step I is monitored by sample analysis of the reaction mixture over time. Generally speaking, Step I is carried out at temperatures of about 125° C. and for periods of about 5 hours. After completion of Step I, Step II is begun by introducing the xylenol component while increasing the temperature of the reaction mixture to about 250° C. The rise in temperature is allowed to occur over a period of about 2.0 hours and then maintained at about 250° C. for approximately 7.5 hours. The course of Step II can be represented by the following chemical equation:

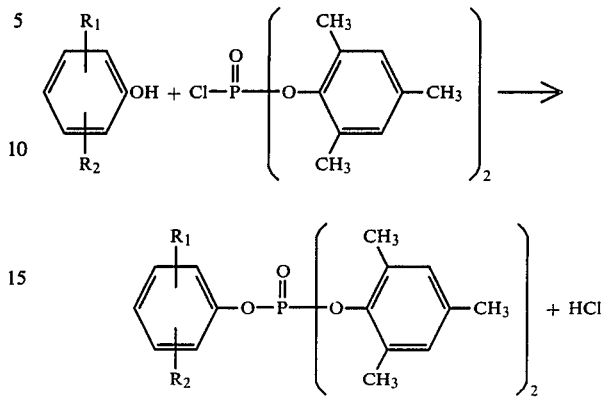

STEP II

After completion of Step II, as evidenced by the absence of any phosphorochloridates in the reaction vessel, the mixture is distilled under vacuum. In a typical run, the product cut was collected boiling at about 230° C. to 260° C. at 1-2 mm/Hg. Reaction times and temperatures can, of course, be varied but those falling generally in the ranges aforesaid are believed to constitute optimum or near optimum conditions insofar as providing maximum yield of desired phosphate ester with minimal decomposition and/or formation of unwanted by-products. Although the xylenol component could be derived by mixing the individual isomers, a preferred source is a low-cost xylenol blend which is commercially available as a chemical by-product. A typical assay of this material is given in Table I. As can be observed, only a minuscule amount of 2,6-xylenol is present.

One of the advantages of the herein phosphate ester flame retardants stems from the fact that they are essentially free of the 2,6-isomer which is believed to be the most toxic of the xylenyl phosphates.

The use of 2,6-free xylenols is further advantageous in that it gives rise to a cleaner reaction in Step II. Apparently, 2,6-xylenol is less reactive than the other xylenol isomers. The cause for this diminished reactivity is thought to be attributable to steric factors. Thus, in 2,6-xylenol, the phenolic function is crowded by the presence of adjacent methyl groups and is thereby less available for reacting with the mesityl phosphorochloridate. As a consequence, more rigorous conditions are required in conducting Step II wherein the xylenol component contains appreciable quantities of the 2,6-isomer. More drastic reaction media, however, tends to favor the formation of decomposition and/or the unwanted by-products. Such extraneous products can seriously impair the properties of the phosphate ester. For instance, these impurities may migrate or vaporize from the resin leading to problems with stress cracking, particularly when incorporating the phosphate into the resin. Problems with stress cracking can also arise if the phosphate ester contains appreciable quantities of the relatively volatile trixylenyl phosphate. However, the formation of this component is virtually eliminated by employing the two-step reaction process of the invention. Moreover, liquids are more convenient than solids which must be melted prior to mixing with the resin. Solid fire retardants are also objectionable in that they tend to crystallize in the resin which may suffer a reduction in impact strength.

A still further advantage of the herein mixtures of lower alkyl substituted triphenyl phosphate flame retardants is their high degree of liquidity. This is due primarily to the large number of isomeric xylenyl moieties in the phosphate ester and the concomitant depression of its melting point.

The invention is further illustrated by the following examples.

EXAMPLE I

A two liter, three-necked flask equipped with stirrer, Y tube, addition funnel, thermometer and condenser was set up and sparged with nitrogen. One thousand grams of mesitol (2,4,6-trimethylphenol) were charged to the flask along with 10.0 grams of anhydrous aluminum chloride catalyst. The mixture was heated to 120° C. and POCl₃ added over a period of two hours.

The reaction was held at 120° C. for two hours until there was no dichloromesityl phosphate in the mixture as evidenced by gas chromatograph analysis.

One hundred and seventy-seven grams of CA33LO (mixed xylenols) were added to the reaction mixture which was then heated to 250° C. over two hours. The run was held for seven hours at 250° C. before it was finished. Reaction completion was determined by the absence of any phosphorochloridates in the mixture.

The crude product consisted (by weight) of 16.8% mesitol and 83.2% ester. On distillation in vacuo, a product cut boiling at 254°–260° C. at 1.8 mm/Hg was obtained. The distribution of esters (% by weight) in the product was as follows:

| XXX | XXM | XMM | MMM |
| --- | --- | --- | --- |
| 1.6% | 18.5% | 23.7% | 56.0% |

The CA33LO is the designation for the xylenol component, the composition of which is set forth in Table I.

EXAMPLE II

Three hundred and forty-five grams of 8093 mesitol were charged to a one liter, three-necked flask equipped with stirrer, thermometer, Y tube, condenser and addition funnel. Two (2.0) grams of anhydrous AlCl₃ (aluminum chloride) were added as catalyst and the pot was heated to 120° C. while under a N₂ pad. The POCl₃ (149 grams) was then added dropwise to the mesitol over a two hour period. The pot temperature was raised to 180° C. and held for 4 hours. The temperature was then reduced to 120° C. and 61.0 grams of CA33LO xylenol were added over a one hour period. The temperature was then raised slowly to 250° C. Six hours after the CA33LO addition the run was finished as evidenced by the absence of any phosphorochloridates in the crude reactor mixture. The crude product weighed 443 grams and consisted of 10% mesitol and 87.26% ester. Distillation under vacuum yielded 364 grams of a product cut boiling at 230°–257° C. at 1.8 mm/Hg. The distribution of esters was as follows:

| XXX | XXM | XMM | MMM |
| --- | --- | --- | --- |
| 2.45 | 19.56 | 27.54 | 47.95 | where X and M have the values defined in Example I.

The 8093 is the trade designation for a commercial grade of mesitol. Its assay is set forth in Table II. This material is sold by the General Electric Company.

EXAMPLE III

The apparatus for the reaction consisted of a 22 liter, three-necked round bottom flask heated with a heating mantle. The flask was equipped with a stirrer, thermometer, condenser, Y tube, and a 2000 ml addition funnel. The vent on the condenser was connected to a caustic scrubbing column to scrub the HCl gas by-product and convert it to sodium chloride. The system was purged with nitrogen prior to charging. Twelve thousand seven hundred and one grams (94.72 moles) of 8093 mesitol were melted (80° C.) and charged to the 22 liter flask. Then 149.0 grams of anhydrous aluminum chloride were charged as catalyst. The system, under a slight nitrogen purge, was then heated to 120° C.

When the temperature of the material in the flask reached 120° C., the POCl₃ addition was started and a total of 5502 grams (35.88 moles) were added over a period of 2.0 hours. The reaction mixture was then analyzed every half hour to determine its composition. Present in the pot were primarily dichloromesityl phosphate, chlorodimesityl phosphate, trimesityl phosphate ester and excess mesitol. When the gas chromatograph analysis of the pot mixture showed that there was no longer any of the dichloridate present, the CA33LO xylenol addition was started. Twenty-two hundred and sixty-two grams (18.52 moles) were added to the flask over a 90 minute period. Following this, the reaction temperature was increased to 250° C. over a three hour period. The analyses of the reaction mixture continued once an hour until all traces of the monochloridate had disappeared. This took about 6 to 8 hours at 250° C. The material was then weighed (16,354 grams), analyzed (14.0% mesitol, 86.0% ester) and transferred to a second 22 liter flask set up for distillation.

PROCEDURE FOR DISTILLING CRUDE ESTER

The crude ester (16,354 grams) was placed in a 22 liter flask equipped with a thermometer and a one-stage Koch Sulzer column, two inches in diameter. The column was topped with a simple Claisen head, condenser and receiving flask. The system was set up to operate at a pressure of 2.0 mm/Hg. The pressure was reduced on the system and heat was applied to the mantle. The material started distilling over at a temperature of 118° C. in the overhead and 165° C. in the pot. The mesitol in the reaction mixture distilled over first and then the ester product started coming over at 268° C. in the overhead and 290° C. in the pot. A heads cut was taken that consisted of 93% mesitol and 6.45% ester. Following the heads cut, the product ester was distilled over at a temperature of 268°–272° C. in the overhead and 290°–292° C. in the pot at 1.8–2.0 mm/Hg pressure. Thirteen thousand four hundred and seven grams of distilled product were obtained. A residue of 1228 grams remained in the flask after the distillation. The product distribution was as follows:

| XXX | XXM | XMM | MMM |
|---|---|---|---|
| 3.01 | 15.02 | 23.97 | 55.60 | wherein X and M have the values defined in the previous examples.

Table III summarizes the course of the reaction for this example.

PREPARATION OF FLAME RETARDANT

The herein mixture of lower alkyl substituted triphenyl phosphates is incorporated in the polyphenylene ether-styrene resin in the known manner of formulating fire retardant thermoplastic polymer compositions. First a dry blend of the powdered resin and additive is prepared. The dry blend is then fed into the twin screw extruder at preselected temperatures. The resin and additive are melt compounded inside the extruder where the temperature and mixing screw plasticate and mix the ingredients. The molten compound exits through a nozzle and immediately enters a cooling bath (water) and then chopped to give pellets. Typically, 10 to 20 parts of phosphate ester per 100 parts of resin are used. Mixing is conveniently effected in a Brabender type mixer (Haake Rheomix Model 600 with Reocord EU10 attachment, manufactured by Haake, Inc., 244 Saddle River Road, Saddle Brook, NJ 07662). Blending of the ingredients takes place at 265° C.

TEST PROCEDURES

Flame Retardancy Tests

The procedure employed is the Underwriters Laboratory (UL)-Subject 94 vertical burn test in which a sample (5.0×0.5 in.) is exposed vertically to a Bunsen burner flame for 10 seconds. The sample is ignited at the bottom and burns up. If the specimen self-extinguishes within 30 seconds, another 10 second application is made. Flaming droplets are allowed to fall on dry absorbent surgical cotton located 12 inches below the sample. If the average burning time for ten samples is less than 5 seconds and the drips do not ignite the cotton, the material is classified 94V-0. If the time is less than 25 seconds and the drips do not ignite the cotton, the material is classified 94V-1. If the sample is self-extinguishing but the cotton is ignited, the material is classified as 94V-2.

Stress Cracking Test

The specimens (Noryl ®) used in the stress cracking test are injection molded. The dimensions are 2.5"×0.5"×0.125". The Noryl bar is bent and placed in the stress jig to give approximately 1% strain. Liquid plasticizer or flame retardant to be evaluated is brushed over the middle 0.5" of the bar. Time to first visible crack and complete failure of the bar are recorded. The test is performed at room or elevated temperature.

The styrene modified polyphenylene ether resins containing the mixed phosphate esters of the invention exhibited the top flame resistance rating of V-0. In stress cracking tests of such resins, the first visible cracks appeared after about 300 hours. Under identical test conditions, commercial aryl phosphate flame retardants stress cracked after about 30 minutes.

TABLE I

| ANALYSIS OF XYLENOL FEEDSTOCK | |
|---|---|
| COMPONENT | AREA % |
| Phenol | 0.14 |
| O—Cresol | 0.09 |
| P—Cresol | 0.22 |
| M-Cresol | 0.67 |
| 2,6-Xylenol | 0.10 |
| 2,4-Xylenol | 16.1 |
| 2,5-Xylenol | 18.2 |
| 2,3-Xylenol | 7.33 |
| 3,4-Xylenol | 5.29 |
| 3,5-Xylenol | 13.6 |
| O—Ethyl Phenol | 0.50 |
| P—Ethyl Phenol | 7.53 |
| M-Ethyl Phenol | 21.6 |
| 2,4,6-TMP (Mesitol) | 0.54 |
| 2,4,5-TMP | 0.23 |
| 3,4,5-TMP | 0.04 |
| 2,3,6-TMP | 1.78 |
| 3-Ethyl-5-Methylphenol | 1.65 |
| Total Identified Components | 95.6% |
| Total Unidentified Components (14 peaks ranging from 0.04 to 1.53%) | 4.4% |

This material is sold by the Merichem Company under the designation Cresylic Acid No. 33LO (CA33LO).

TABLE II

| 8093 MESITOL SPECIFICATION[1] | | |
|---|---|---|
| ISOMER | SPECIFICATION | TYPICAL |
| Phenol | 3 Max. | Trace |
| Ortho-Cresol | 3 Max. | <1.0 |
| 2,6 Xylenol | 3 Max. | <1.0 |
| 2,4/2,5 Xylenol | 3–12 | 6–8 |
| 2,4,6 Trimethylphenol | 80–93 | 89 |
| 2,3,6 Trimethylphenol | — | 1.5 |
| Unidentified | — | 2.5 |
| OTHER PROPERTIES | | |
| Moisture Content | 0.3% Max. | |
| Non-Volatiles | 0.5% Max. | <0.2 |
| Color | C-3 Max. | |
| TYPICAL PROPERTIES (Not Binding) | | |
| Flash Point (TOC) | | 185° F. |
| Freezing Point Range | | 60°–75° C. |
| Boiling Point Range | | 190°–250° C. |
| Specific Gravity at 60° C. | | 8.3 lbs./gal. |

[1]Sold by the General Electric Company

TABLE III

| GC ANALYSIS OF REACTION MIXTURE RUN OF EXAMPLE III | | | | | | | | | |
|---|---|---|---|---|---|---|---|---|---|
| Time, Hours | Pot Temp. °C. | Remarks | Sample No. | Xylenol | Mesitol | CA33LO | Dichlorodate | Monochloride | Total Ester |
| 0 | 120° C. | Start POCl$_3$ | 1 | 7.50 | 92.41 | — | — | — | — |
| 2.6 | 120° C. | POCl$_3$ Addition Complete | 3 | — | 48.33 | — | 1.25 | 26.0 | 22.38 |
| 3.6 | 127° C. | — | 4 | — | 39.80 | — | — | 47.01 | 7.50 |
| 4.0 | 126° C. | — | 5 | — | 39.76 | — | — | 50.40 | 9.54 |
| 4.2 | 126° C. | Start CA33LO | 6 | — | 34.36 | — | Trace | 55.28 | 10.32 |
| 6.0 | 126° C. | CA33LO Addition | 8 | — | 29.04 | 4.36 | — | 43.44 | 21.40 |

TABLE III-continued
GC ANALYSIS OF REACTION MIXTURE RUN OF EXAMPLE III

| Time, Hours | Pot Temp. °C. | Remarks | Sample No. | Xylenol | Mesitol | CA33LO | Dichloro- date | Mono- chloride | Total Ester |
|---|---|---|---|---|---|---|---|---|---|
| | | Complete | | | | | | | |
| 6.5 | 150° C. | — | 9 | — | 27.20 | 1.85 | — | 42.01 | 27.31 |
| 7.0 | 175° C. | — | 10 | — | 30.98 | .32 | — | 32.26 | 36.44 |
| 8.0 | 200° C. | — | 11 | — | 30.29 | — | — | 21.52 | 48.19 |
| 9.0 | 250° C. | — | 13 | — | 25.96 | — | — | 9.26 | 64.76 |
| 10.0 | 254° C. | — | 14 | — | 18.99 | — | — | 4.97 | 75.96 |
| 11.0 | 257° C. | — | 15 | — | 16.56 | — | — | 2.24 | 81.15 |
| 12.0 | 252° C. | — | 16 | — | 14.68 | — | — | 1.31 | 84.01 |
| 13.0 | 256° C. | — | 17 | — | 13.85 | — | — | 0.76 | 85.36 |
| 14.0 | 255° C. | — | 18 | — | 13.64 | — | — | 0.44 | 85.93 |
| 15.0 | 255° C. | — | 19 | — | 12.59 | — | — | 0.22 | 86.98 |
| 16.0 | 251° C. | — | 20 | — | 13.15 | — | — | Trace | 86.83 |
| 17.0 | 254° C. | — | 21 | — | 13.76 | — | — | — | 86.25 |

What is claimed is:

1. A liquid mixture of lower alkyl substituted triphenyl phosphates consisting essentially of the following components (by weight):

(a) about 1.5% to about 3.0% of:

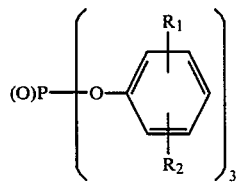

(b) about 15.0% to about 20.0% of:

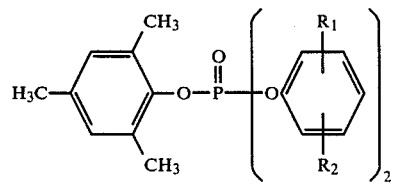

(c) about 23.0% to about 28.0% of:

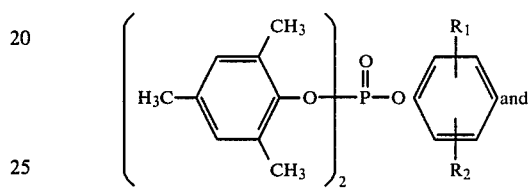

(d) about 47.0% to about 56.0% of:

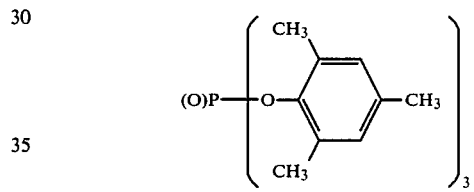

wherein $R_1$ and $R_2$ are each selected from the class consisting of hydrogen, methyl and ethyl, it being understood that when one of $R_1$ and $R_2$ is hydrogen the other is ethyl and when one of $R_1$ and $R_2$ is methyl the other is methyl, the resulting two methyl groups being in the 2,4-, 2,5-, 2,3-, 3,4- and 3,5-positions, it being further understood that the ethyl groups are almost entirely in the meta (m) and para (p) positions.

2. A fire retardant composition having high resistance to stress cracking comprising a polyphenylene ether-polystyrene resin and as a fire retardant therefor the mixture of lower alkyl substituted triphenyl as defined in claim 1.

3. The fire resistant composition of claim 2 containing by weight about 10 to 20 parts of the lower alkyl substituted triphenyl phosphate per 100 parts of resin.

4. The fire resistant composition of claim 1 wherein the resin is composed by weight of 55% polyphenylene ether and 45% polystyrene.

* * * * *